United States Patent
Matson

[19]

[11] Patent Number: 6,064,917
[45] Date of Patent: May 16, 2000

[54] METHOD FOR THREE-DIMENSIONAL, INHOMOGENEITY LOCALIZATION IN TURBID MEDIUM USING DIFFUSE PHOTON DENSITY WAVES

[75] Inventor: Charles L. Matson, Albuquerque, N.Mex.

[73] Assignee: The United States of America as represented by the Secretary of the Air Force, Washington, D.C.

[21] Appl. No.: 08/995,724

[22] Filed: Dec. 22, 1997

[51] Int. Cl.[7] .................................................. G06F 19/00
[52] U.S. Cl. .......................... 700/90; 600/407; 600/425; 600/473
[58] Field of Search ................. 700/90; 702/19; 600/407, 473, 425

[56] References Cited

U.S. PATENT DOCUMENTS

| | | | |
|---|---|---|---|
| 4,562,540 | 12/1985 | Devaney | 700/90 |
| 4,594,662 | 6/1986 | Devaney | 700/90 |
| 4,598,366 | 7/1986 | Devaney | 700/90 |
| 4,920,498 | 4/1990 | Kaneko | 204/546 |
| 5,070,455 | 12/1991 | Singer et al. | 378/196 |
| 5,203,339 | 4/1993 | Knuttel et al. | 600/425 |
| 5,309,912 | 5/1994 | Knuttel | 600/425 |
| 5,353,799 | 10/1994 | Chance | 600/473 |
| 5,416,582 | 5/1995 | Knutson et al. | 356/349 |
| 5,483,441 | 1/1996 | Scofield | 700/90 |
| 5,807,263 | 9/1998 | Chance | 600/476 |
| 5,930,384 | 7/1999 | Guillemaud et al. | 382/154 |
| 5,931,789 | 8/1999 | Alfano et al. | 600/473 |
| 5,941,827 | 8/1999 | Papaioannou | 600/473 |

OTHER PUBLICATIONS

Three–dimensional tumor localization in thick tissue with the use of diffuse photon–density waves (Charles Matson et al., pp. 215–216).

*Primary Examiner*—William Grant
*Assistant Examiner*—Zoila Cabrera
*Attorney, Agent, or Firm*—Stanton E. Collier

[57] ABSTRACT

Three dimensional localization of a cancer tumor is performed by amplitude-modulated optical radiation producing a time varying photon distribution in the body of the patient examined. The amplitude and phase of the diffuse photon density wave (DPDW) are measured in the detection plane and a novel algorithm is employed enabling three-dimensional tumor localization to occur with only one measurement and without the need for a moving radiation scanner.

38 Claims, 2 Drawing Sheets

METHOD FOR THREE-DIMENSIONAL, INHOMOGENEITY LOCALIZATION IN TURBID MEDIUM USING DIFFUSE PHOTON DENSITY WAVES

STATEMENT OF GOVERNMENT INTEREST

The present invention may be manufactured and used by or for the Government for governmental purposes without the payment of any royalty thereon.

BACKGROUND OF THE INVENTION

The use of optical radiation for imaging human tissue has many desirable advantages over other imaging methodologies but can require additional complexity in the processing methodology. Although optical radiation can penetrate human tissue reasonably well in the optical and near infrared wavelength regimes, strong scattering in thick tissue results in most of the illuminating light being scattered. As a result, standard tomographic and imaging methodologies provide poor image information. To extract the highest-possible quality in the images, the scattered light must be used or blocked. As early as 1929, light was used to diagnose breast lesions but the scattered light was viewed as noise obscuring the image. The early-arriving photons were viewed as producing the desired high-accuracy two-dimensional tumor localization, while the scattered photons blurred this information. Much later, a similar approach was used to screen for breast cancer. Again, scattered light was viewed as an undesirable artifact. Time-resolved techniques use time-gating to collect the unscattered and minimally-scattered light while screening out the rest of the scattered light. Although these techniques require very short picoseconds to femtoseconds pulses and correspondingly fast detection systems, they have been used to obtain three-dimensional images. Another technique used to discriminate against scattered light is optical coherence tomography which utilizes low coherence interferometry to gate out multiply-scattered light. This method has been used in tissues with thicknesses up to tens of mean scattering lengths.

Another promising category of approaches, called frequency domain methods, utilize diffuse photon density waves (DPDWs) for illumination. These methods explicitly use the scattered light and neglect the unscattered light to image thick tissue. Generally speaking, methods that have been suggested that use DPDWs for illumination are used either for two-dimensional mammography or are tomographic in nature. This usually necessitates movement of the source/detector setup or the tissue samples to obtain depth information, which poses alignment as well as convenience problems when implementing in vivo imaging in a clinical environment. A notable exception is a method which obviates the need for mechanical movement by using multiple sources phased in an appropriate way to scan a spot of high or low photon density throughout the tissue. Thus, a novel method is desired for localizing inhomogeneities in three dimensions employing optical probing radiation to minimize health risks when probing human tissue, and which requires no mechanical movement of the equipment, and that greatly increases the accuracy to which inhomogeneities can be localized. The benefit of such a desired method is that, when used for breast cancer detection, existing mammographic procedures can be used. This can enable quicker acceptance and understanding of the method for use in a clinical environment. Although the optical mammography application of this method is a primary use, this method can be used for localizing inhomogeneities in a wide variety of turbid medium. For example, the invention may be practicable for the detection of pockets of precious commodities such as oil, natural gas and metallic ores. The method of the present invention is an improvement upon previous diffraction tomography systems utilizing a Green's function, whose Fourier transform is purely phase. See U.S. Pat. Nos. 4,594,662, 4,598,366 and 4,562,540 issued to A. J. Devaney and incorporated by reference herein.

BRIEF SUMMARY OF THE INVENTION

The present invention uses a Green's function which has a Fourier transform that has both amplitude and phase variations as a function of spatial frequency. As will be shown, it is the amplitude of the Fourier transform of the Green's function which provides the means to localize inhomogeneities, not the phase. In addition, diffraction tomographic systems inherently assume weak scattering and absorption properties for the inhomogeneities, i.e., the Born or Rytov approximations. In contrast, the invention works equally well for weak or strong inhomogeneity properties. The method broadly involves Fourier transforming the scattered return radiation component detected at a photosensor detection plane, establishing the location of a first reconstruction plane behind the detection plane, dividing the transform of the return radiation by a propagation transfer function, inverse transforming and normalizing to unit energy, repeating these steps for a second and subsequent reconstruction planes and finding the peak amplitude of a reconstructed scattered wave in a particular reconstruction plane to indicate the depth of the tumor, and laterally identifying the tumor position by finding the peak of the reconstructed scattered wave amplitude in the detection plane.

BRIEF SUMMARY OF THE DRAWINGS

The various features and advantages of the invention will become more apparent upon study of the following description, taken in conjunction with the drawings in which.

DETAILED DESCRIPTION OF PREFERRED EMBODIMENTS OF THE INVENTION

Figure 1:
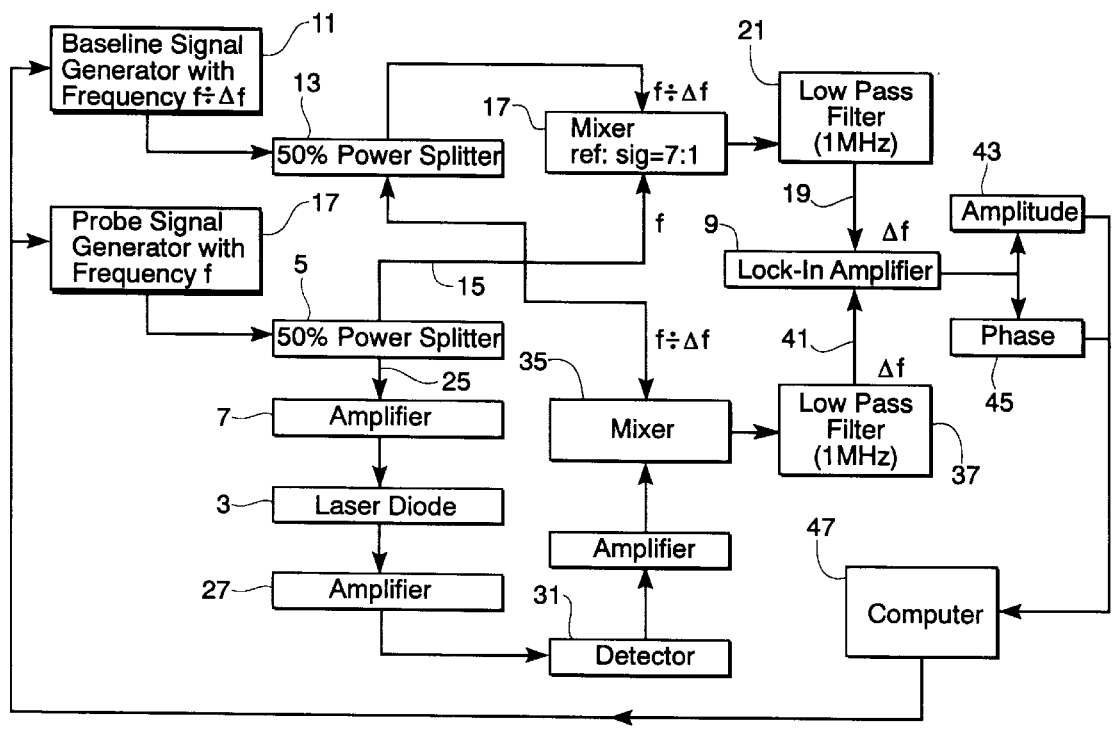
FIG. 1 schematically illustrates our experimental setup for performing the method of the invention.

Previous biomedical imaging work has shown that, in an infinite homogeneous strongly-scattering medium, light transport is well-modeled by the diffusion equation. To create DPDWs, single or multiple light sources are sinusoidally modulated, typically at radio frequencies. Using the diffusion equation, DPDWs can be found as the time-dependent part of the solution. In an infinite homogeneous medium, the solution for a single point light source to the forward problem is a damped spherical outgoing wave. When the medium is infinite but not homogeneous, the problem becomes more challenging. Analytic solutions have been calculated assuming that the deviations from homogeneity consist of spheres, cylinders, and semi-infinite planar boundaries. In addition, perturbative solutions have been obtained for general inhomogeneous medium which include both the forward and inverse problems.

Solutions to the diffusion equation have also been derived to describe the behavior of light propagation in a source-free vacuum. Because the medium is neither scattering or absorbing, solutions describing light propagation from a point source are non-damped spherical waves. In addition, using Fourier analysis, Goodman showed that light propagation in a vacuum can be analyzed using a linear system space-invariant framework. See J. W. Goodman, "Introduction to Fourier Optics", McGraw Hill, San Francisco (1968). It is this framework that we will use to obtain three-dimensional localization of inhomogeneities in an infinite medium. We need to modify Goodman's results to account for scattering effects and to emphasize the solution in the evanescent wave regime where DPDWs are typically implemented.

Let $U(x,y,z)$ be the (complex) mathematical description of the photon density at a point $(x,y,z)$ in an infinite homogeneous medium which has been created by an unspecified collection of sources. Let us further assume that the wave is traveling in the positive z direction. Let $A_o(f_x,f_y)$ be the two-dimensional spatial Fourier transform of $U(x,y,z=0)$ and let $A_z(f_x,f_y)$ be the two-dimensional spatial Fourier transform of $U(x,y,z)$ at some unspecified but positive value of z. Then, following Goodman's free-space derivation, it can be shown that $$A_z(f_x, f_y) = A_o(f_x, f_y)\exp\left\{iz\sqrt{k^2 - (2\pi f_x)^2 - (2\pi f_y)^2}\right\} \quad (1)$$

where k is the photon density wavenumber and $i=\sqrt{-1}$. In Eq.(1) the Fourier transform of the photon density distribution in a plane is related to the Fourier transform of the photon density distribution in a earlier parallel plane by a simple multiplication. Thus, propagation of the photon density wave in a homogeneous medium can be modeled as a space-invariant linear system. The transfer function, $H_z(f_x, f_y)$, describing the wave propagation is given by $$H_z(f_x, f_y) \frac{A_z(f_x, f_y)}{A_o(f_x, f_y)} = \exp\left\{iz\sqrt{\left(\frac{-v\mu_a + i\omega}{D}\right) - (2\pi f_x)^2 - (2\pi f_y)^2}\right\} \quad (2)$$

where we have replaced the first term inside the radical with the definition of k, where v is the speed of light in the medium, $\mu_a$ is the absorption coefficient, $\omega$ is the (radian) frequency of the photon density wave, $D=v[3(\mu'_s+\mu_a)]^{-1}$ is the photon diffusion coefficient, and $\mu'_s$ is the reduced scattering coefficient.

In a homogeneous medium, we can reconstruct the photon density in any plane back along the direction of propagation by using this transfer function relationship to invert the propagation process. We accomplish this by taking the amplitude and phase distribution of the scattered photon density wave at our measurement plane, Fourier transforming it, dividing the Fourier transform by the transfer function that corresponds to the distance z that we are interested in, and inverse Fourier transforming to get the scattered wave. However, this is only quantitatively valid in a homogeneous medium. Consider now a homogeneous medium with a spherical inhomogeneity. This heterogeneous medium can be modeled as the homogeneous medium with singularities located at the center of the sphere. The linear systems theory approach to reconstructing the detected photon density wave is quantitatively valid only up the plane which contains the singularities. However, the reconstructed photon density wave in the volume peaks at the location of the singularities. This peak is more clearly detected by normalizing each reconstructed plane to unit energy so that the overall depth-dependent exponential attenuation due to the background medium is removed. Therefore, we can localize the singularities in depth by identifying the location of the peak of the amplitude of the normalized reconstructed photon density wave as a function of depth. In addition, we can identify the lateral location of the inhomogeneity by finding the peak of the amplitude of the detected scattered photon density wave. The combination of these two localization steps determines the three-dimensional location of the inhomogeneity from a single two-dimensional planar measurement.

In the interests of clarity and brevity, FIG. 1, illustrating our experimental setup, shows only one channel for both illumination and detection. In general, multiple laser diodes will be used for illumination, and detection will usually be accomplished with a photo detector array. Thus, the operation of only one of these channels will be described. Referring to FIG. 1, we first generate a radio frequency wave of the desired frequency using probe signal generator 1. The probe signal will be used to modulate our illumination laser diode 3 via power splitter 5 and amplifier 7. Because we desire to use a lock-in amplifier 9 for detection, we also generate a radio wave whose frequency is offset by tens of kilohertz from the frequency of the probe signal. The second radio wave is generated by the baseline signal generator 11. The baseline signal is used for mixing with both the probe signal and the detected signal in order to heterodyne the radio wave frequencies down to the frequency difference between the probe and baseline signals. We next split both the probe and baseline signals into two equal amplitude components. One of the probe signals at lead 15 is mixed with one of the baseline signals supplied via power splitter 13 at mixer 17 to produce the desired reference input for the lock-in amplifier 9. The reference input signal at 18 is low-pass filtered by filter 21 to remove spurious high-frequency content before being connected to lock-in amplifier 9 via lead 19. The second probe signal at 25 is amplified by amplifier 7 and then used to modulate the laser diode 3 which illuminates the tissue sample 27. On the other side of the tissue, the portion of the laser light which passes through the tissue sample is detected by photodetector 31. The detected signal is then amplified by amplifier 33, mixed with the second component of the baseline signal by mixer 35, low-pass filtered by 1 Mhz filter 37, and fed into lock-in amplifier 9 via lead 41. The output of lock-in amplifier 9 is the amplitude and phase of the detected signal relative to the amplitude and phase of the baseline signal. The amplitude and phase represented symbolically by 43 and 45 are fed into computer 47, which serves both to control the aforesaid equipment and to accomplish data processing in accordance with the method of the invention.

For our reconstruction algorithm executed by computer 47, we desire to obtain a grid of equally-spaced measurements in a plane. There are several methods by which we obtain the desired planar set of measurements. The first method is accomplished mounting a single detector on a translation stage and using the computer to control the detector movement. This is the simplest means of implementing our system concept. A second method is to duplicate the one-channel system shown in FIG. 1 for the desired number of channels, with the exception of using just one computer. A third method is to duplicate the part of the instrumentation system from the detector through the second mixer, and then use a digitally-controlled electronic switch-box to scan through all the detector outputs and input them into the lock-in amplifier. These variations are obvious equivalents well known to those skilled in the art.

Figure 3:
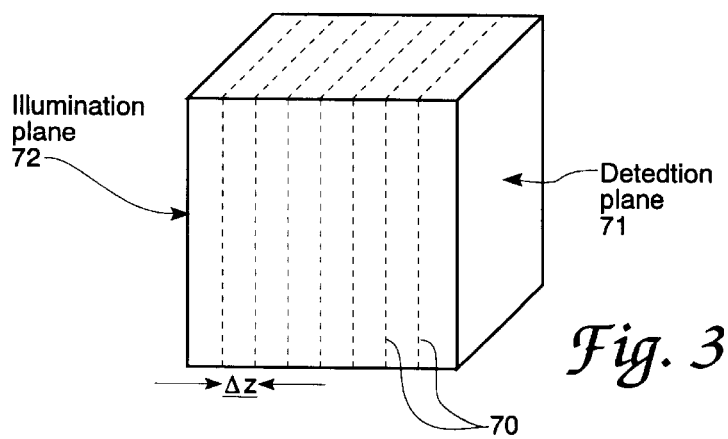
FIG. 3 schematically illustrates the reconstructed turbid medium volume.
Figure 2:
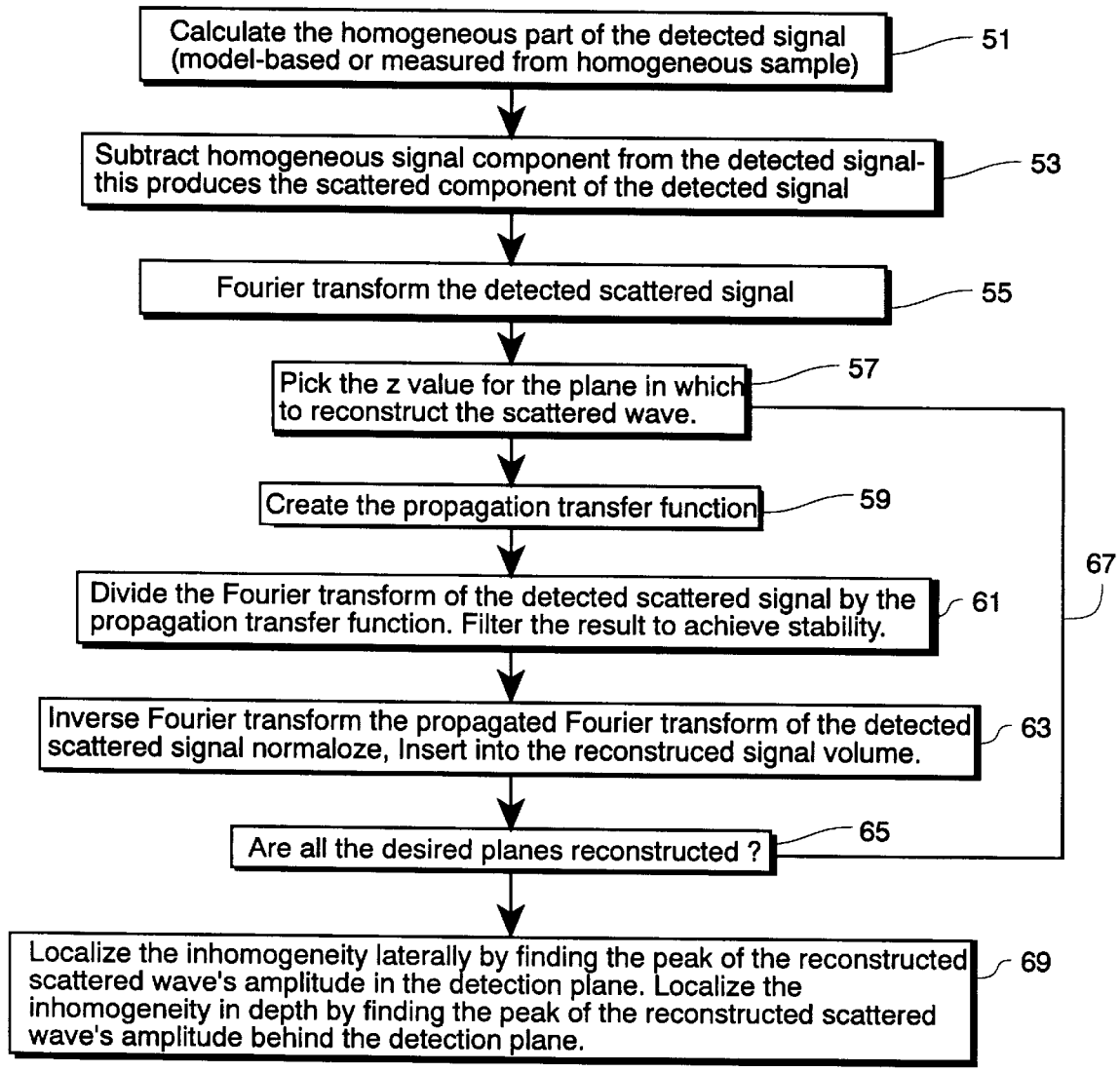
FIG. 2 illustrates a flow chart, describing the computer algorithm for performing the method of the invention.

FIG. 3 schematically illustrates the reconstructed turbid medium volume. Illumination plane 72 can contain a flat rectangular array of light emitting laser diodes while detection plane 71 can contain a corresponding array of light detecting photodiodes, in accordance with prior art arrangements. Dashed lines 70 represent the planes where the photon density wave is reconstructed, and are separated by incremental changes in the z parameter associated with block 57 of the flow chart to be discussed. We now describe our algorithm which is used to reconstruct the scattered wave throughout the tissue volume by reconstructing planar slices of the volume taken parallel to the detection plane at desired locations using Eq.(2). A flowchart of the algorithm is shown in FIG. 2. The first step of the algorithm is to calculate the homogeneous portion of the detected signal, because the detected signal is the sum of the scattered wave and the detected wave, block 51. To calculate this part of the detected signal, the background properties of the medium, $\mu_a$ and D, are needed. Bulk properties of the background medium are either directly measured (for example, using a non-inhomogeneity-bearing breast) or estimated from the medium with the inhomogeneity. From these properties, the homogeneous part is calculated and subtracted from the detected signal at 53. The resulting signal is the scattered portion of the detected signal, which is then Fourier transformed at 55. Next, the value of z which corresponds to the plane in which we desire to reconstruct the scattered wave is determined at 57. Using Eq.(2), we calculate the propagation transfer function at 59. To calculate this transfer function, we need the background $\mu_a$ and D values (determined in the homogeneous wave step). Once the propagation transfer function is calculated, the Fourier transform of the detected scattered wave is divided by this propagation transfer function at 61. The result is multiplied by a stabilizing filter. A filter is desired because of the shape of the transfer function shown in Eq.(2). Near zero spatial frequency ($f_x=f_y=0$) the transfer function is flat. For very large values of $f_x$ and/or $f_y$, the transfer function has an exponential decay. Between these two regions the transfer function transitions from being flat to decaying exponentially. The exponential decay portion of the transfer function results in underflow and overflow computer problems even if the data is noise-free. We pick the filter to pass all spatial frequency values where the transfer function is either flat or transitioning between the flat region and the exponential decay region. It is critical to include more than just the transfer function's flat region because it is precisely this amplitude variation that provides the localization effect. If just the phase of the transfer function is used, as is done in standard diffraction tomography, localization cannot be accomplished. More accurate localization occurs when more of the transfer function is included, but this also makes the algorithm more sensitive to noise. Therefore, this is a user-adjustable parameter to accommodate system noises. Once the filtering is accomplished, the result is inverse Fourier transformed, normalized to unit energy, and inserted into the reconstructed scattered wave volume array at block 63. At this point, the algorithm checks at block 65 to see if all the desired planes have been reconstructed. If not, the algorithm loops back via 67 to the point where the location of the next plane to be reconstructed is selected at 57 by incrementing the value of z, and the planar reconstruction begins again. If and when the entire volume is reconstructed, the algorithm moves to the last step, where the inhomogeneity is localized both laterally and in depth at 69. To accomplish this localization, first the amplitude of the normalized reconstructed scattered wave is calculated. The lateral localization is accomplished by determining the maximum value of the scattered wave in the detection plane, while the depth localization is accomplished by determining the maximum value of the scattered wave behind the detection plane.

Although our algorithm reconstructs inhomogeneity locations for weak or strong perturbations, a diffraction tomographic theory has been developed, for weak perturbations, which accurately predicts the performance of our algorithm. See C. L. Matson and H. Liu "Analysis of the Forward Problem with Diffuse Photon Density Waves in Turbid Medium using a Diffraction Tomographic Model" submitted to IEEE Transactions on Image Processing, October 1997. This analysis extends the qualitative nature of the above explanation to quantitatively predict the structure of the reconstructed three-dimensional volume. A key aspect of this reconstruction algorithm is that radio-frequency DPDWs are not necessary for accurately recovering the location of the inhomogeneity. Computer simulations have been conducted which show that DPDWs of just a few hertz can be used for the reconstruction. This greatly simplifies the hardware requirements, thus lowering costs.

It should now be appreciated that advantageously, a single set of two-dimensional measurements can be used to provide three-dimensional inhomogeneity localization. Knowledge of the propagation parameters in the medium is what allows us to recreate the third dimension from the measured two-dimensional data. Previous methods require many two-dimensional measurements, with or without mechanical movement of the equipment, to provide the three-dimensional information. Another major new feature of this invention is that the processing algorithm is linear. This enables dramatically faster reconstructions of inhomogeneity locations than is currently available. This will benefit the cost-effectiveness of the procedure because the data processing time is much less. In addition, because of the speed of the processing algorithm, time-varying characteristics can be monitored much more frequently than when using previous methods. Still another new feature is that this invention incorporates improvements from previous inventions to enhance its performance. For example, disclosed systems in U.S. Pat. Nos. 5,309,912 and 5,491,552 issued to Knuttel, use special illumination methods to highlight specific locations in the turbid medium. The present invention can take advantage of these illumination methods with the disclosed data-processing methodology to enhance inhomogeneity localization. However, this method does not require such special illumination methods, so cheaper and faster illumination methods can also be used, giving the practitioner a choice between cost and performance when implementing this invention.

Further details pertaining the present invention may be obtained from our published paper, incorporated by reference herein. See Charles Matson et al., "Three-dimensional Tumor Localization in Thick Tissue using Diffuse Photon Density Waves", Applied Optics, January 1997.

Variations in the foregoing description of the method of the invention will be apparent to the skilled worker in the art and thus the scope of the invention is to be limited solely by the terms of the following claims and art recognized equivalents thereof. For example, the invention can also be implemented in a reflective mode. All the previous discussions assume that the detected light is measured on the opposite side of the turbid medium to where the illumination is applied. Taking into account the characteristics of the inhomogeneities in the medium, the reflected light can be used to accomplish the inhomogeneity localization. This invention can also be implemented without using radio frequency probe signals. This removes the need for expensive signalgeneration equipment as well as the heterodyning hardware and hence permits a much lower cost system to be built. Equivalent transforms, well known to skilled workers in the art, may be used in place of Fourier transforms.

Also, the present invention can be applied to exploration of natural resources using sonic radiation employed in the aforesaid reflection mode. Sonic transmitters would be placed in a two-dimensional grid along with potentially collocated sonic detectors. Return signals would consist of both the homogenous portion and the portion scattered from pockets of buried resources to be located. The skilled worker in the art would readily appreciate that by following the aforesaid method of the invention, the three-dimensional location of the resource can be determined.

What is claimed:

1. Method of detecting the location of inhomogeneities in three dimensions in a turbid medium by analyzing a scattered wave returned by said medium comprising the steps of:
   (a) projecting into said turbid medium electromagnetic radiation having a time varying pattern of photon density capable of being scattered and absorbed while migrating in said turbid medium;
   (b) retrieving in a detection plane a detected electromagnetic signal, which has passed through said medium in accordance with step (a), indicative of said inhomogeneities;
   (c) computer processing said detected signal by
      (c-1) calculating a homogeneous signal component of said detected signal;
      (c-2) subtracting said homogeneous signal component from said detected signal for producing a scattered component of said detected signal;
      (c-3) Fourier transforming said scattered component to produce a transform of the detected scattered component;
      (c-4) selecting a location of a reconstruction plane in which to reconstruct the scattered wave;
      (c-5) dividing the transform of the detected scattered component produced in accordance with step (c-3) by a propagation transfer function
      (c-6) stability filtering the result of the performance of step (c-5);
      (c-7) inverse Fourier transforming a signal produced in accordance with step (c-6) to produce a transformed signal;
      (c-8) inserting said transformed signal resulting from performance of step (c-7) into a reconstructed signal volume plane;
      (c-9) repeating steps (c-2) through (c-8) until a given plurality of reconstruction planes are reconstructed;
      (c-10) localizing an inhomogeneity in depth by finding a peak of a reconstructed scattered wave's amplitude in a reconstruction plane behind the detection plane; and
      (c-11) localizing an inhomogeneity laterally by finding a peak of the reconstructed scattered wave amplitude in said detection plane.

2. The method of claim 1 wherein step (c-6) employs a pillbox filter.

3. The method of claim 1 wherein step (a) projects said electromagnetic radiation into human flesh.

4. The method of claim 1 including normalizing said transformed signal of step (c-7).

5. Method of detecting the location of inhomogeneities in a turbid medium by analyzing a scattered wave returned by said medium comprising the steps of:
   (a) projecting into said turbid medium electromagnetic radiation having a time varying pattern of photon density capable of being scattered and absorbed while migrating in said turbid medium;
   (b) retrieving in a detection plane a detected electromagnetic signal, which has passed through said medium in accordance with step (a), indicative of said inhomogeneities;
   (c) computer processing said detected signal by
      (c-1) calculating a homogeneous signal component of said detected signal;
      (c-2) subtracting said homogeneous signal component from said detected signal for producing a scattered component of said detected signal;
      (c-3) Fourier transforming said scattered component to produce a transform of the detected scattered component;
      (c-4) selecting a location of a reconstruction plane in which to reconstruct the scattered wave;
      (c-5) dividing the transform of the detected scatter component produced in accordance with step (c-3) by a propagation transfer function
      (c-6) inverse Fourier transforming the signal produced in accordance with (c-5) to produce a transformed signal;
      (c-7) inserting said transformed signal resulting from performance of step (c-6) into a reconstructed signal volume plane;
      (c-8) repeating steps (c-2) through (c-7) until a given plurality of reconstruction planes are reconstructed; and
      (c-9) localizing a inhomogeneity in depth by finding a peak of a reconstructed scattered wave's amplitude in a reconstruction plane behind the detection plane.

6. The method of claim 5 further including localizing a inhomogeneity laterally by finding a peak of the reconstructed scattered wave amplitude in said detection plane.

7. The method of claim 5 including stability filtering the result of the performance of step (c-5) before the performance of step (c-6).

8. The method of claim 5 wherein step (a) projects said electromagnetic radiation into human flesh.

9. The method of claim 2 including normalizing said transformed signal of step (c-6).

10. The method of claim 3 including normalizing said transformed signal of step (c-6).

11. The method of claim 6 wherein step (a) projects said electromagnetic radiation into human flesh.

12. The method of claim 6 including stability filtering the result of the performance of step (c-5) before the performance of step (c-6).

13. The method of claim 12 wherein step (a) projects said electromagnetic radiation into human flesh.

14. The method of claim 12 wherein said stability filtering step employs a pillbox filter.

15. The method of claim 7 wherein said stability filtering step employs a pillbox filter.

16. The method of claim 7 wherein step (a) projects said electromagnetic radiation into human flesh.

17. The method of claim 4 including normalizing said transformed signal of step (c-6).

18. Method of detecting the location of inhomogeneities in three dimensions in a turbid medium by analyzing a scattered wave returned by said medium comprising the steps of:
   (a) projecting into said turbid medium radiation having a time varying pattern of photon density capable of being scattered and absorbed while migrating in said turbid medium;

(b) retrieving in a detection plane a detected return signal, representative of radiation which has passed through said medium in accordance with step (a), indicative of said inhomogeneities;

(c) computer processing said detected return signal by
  (c-1) Fourier transforming said detected signal;
  (c-2) selecting a location of a reconstruction plane in which to reconstruct the scattered wave;
  (c-3) dividing the transform of the detected signal produced in accordance with step (c-1) by a propagation transfer function;
  (c-4) inverse Fourier transforming a signal produced in accordance with step (c-3) to produce a transformed signal;
  (c-5) inserting said transformed signal resulting from performance of step (c-4) into a reconstructed signal volume plane;
  (c-6) repeating steps (c-1) through (c-5) until a given plurality of reconstruction planes are reconstructed; and
  (c-7) localizing an inhomogeneity in depth by finding a peak of a reconstructed scattered wave's amplitude in a reconstruction plane behind the detection plane.

19. The method of claim 18 including the step of localizing an inhomogeneity laterally by finding the peak of the reconstructed scattered wave amplitude in said detection plane.

20. The method of claim 18 including stability filtering the result of the performance of step (c-3) before the performance of step (c-4).

21. The method of claim 19 including stability filtering the result of the performance of step (c-3) before the performance of step (c-4).

22. The method of claim 18 wherein step (a) projects said electromagnetic radiation into human flesh.

23. The method of claim 14 including normalizing said transformed signal of step (c-4).

24. The method of claim 15 including normalizing said transformed signal of step (c-4).

25. The method of claim 19 wherein step (a) projects said electromagnetic radiation into human flesh.

26. The method of claim 16 including normalizing said transformed signal of step (c-4).

27. The method of claim 20 wherein said stability filtering step employs a pillbox filter.

28. The method of claim 20 wherein step (a) projects said electromagnetic radiation into human flesh.

29. The method of claim 27 wherein step (a) projects said electromagnetic radiation into human flesh.

30. The method of claim 21 wherein said stability filtering step employs a pillbox filter.

31. The method of claim 21 wherein step (a) projects said electromagnetic radiation into human flesh.

32. The method of claim 30 wherein step (a) projects said electromagnetic radiation into human flesh.

33. Method of detecting the location of inhomogeneities in three dimensions in a turbid medium by analyzing a scattered wave returned by said medium comprising the steps of:

(a) projecting into said turbid medium radiation capable of being scattered and absorbed while migrating in said turbid medium;

(b) retrieving in a detection plane a detected return signal, representative of said radiation which has passed through said medium in accordance with step (a), indicative of said inhomogeneities;

(c) computer processing said detected return signal by
  (c-1) Fourier transforming said detected signal;
  (c-2) selecting a location of a reconstruction plane in which to reconstruct the scattered wave;
  (c-3) dividing the transform of the detected signal produced in accordance with step (c-1) by a propagation transfer function;
  (c-4) inverse Fourier transforming a signal produced in accordance with step (c-3) to produce a transformed signal;
  (c-5) inserting said transformed signal resulting from performance of step (c-4) into a reconstructed signal volume plane;
  (c-6) repeating steps (c-1) through (c-5) until a given plurality of reconstruction planes are reconstructed; and
  (c-7) localizing an inhomogeneity in depth by finding a peak of a reconstructed scattered wave's amplitude in a reconstruction plane behind the detection plane.

34. The method of claim 33 including the step of localizing an inhomogeneity laterally by finding the peak of the reconstructed scattered wave amplitude in said detection plane.

35. The method of claim 26 including stability filtering the result of the performance of step (c-3) before the performance of step (c-4).

36. The method of claim 26 including normalizing said transformed signal of step (c-4).

37. The method of claim 27 including normalizing said transformed signal of step (c-4).

38. The method of claim 27 including stability filtering the result of the performance of step (c-3) before the performance of step (c-4).

* * * * *